US007320437B2

(12) United States Patent
Anderson et al.

(10) Patent No.: US 7,320,437 B2
(45) Date of Patent: Jan. 22, 2008

(54) DEVICE FOR DISPENSING LIQUID

(75) Inventors: Garth Anderson, Hamilton (NZ); Shaun Plant, Hamilton (NZ); Cornelis Klein, Hamilton (NZ)

(73) Assignee: Instrument Supplies Limited, Hamilton (NZ)

( * ) Notice: Subject to any disclaimer, the term of this patent is extended or adjusted under 35 U.S.C. 154(b) by 224 days.

(21) Appl. No.: 10/467,778

(22) PCT Filed: Feb. 26, 2002

(86) PCT No.: PCT/NZ02/00022

§ 371 (c)(1),
(2), (4) Date: May 4, 2004

(87) PCT Pub. No.: WO02/067808

PCT Pub. Date: Sep. 6, 2002

(65) Prior Publication Data

US 2004/0195382 A1 Oct. 7, 2004

(30) Foreign Application Priority Data

Feb. 12, 2001 (NZ) ..................................... 509851

(51) Int. Cl.

*A62C 15/00* (2006.01)
*B05B 9/08* (2006.01)
*B05B 9/06* (2006.01)
*A61M 31/00* (2006.01)

(52) U.S. Cl. ........................ 239/154; 239/526; 239/61; 239/152; 239/9; 604/67; 604/186; 604/191

(58) Field of Classification Search ................ 239/525, 239/526; 600/431; 119/656, 174; 604/246, 604/67, 191, 186; 433/27, 80; 222/63, 52, 222/71, 73

See application file for complete search history.

(56) References Cited

U.S. PATENT DOCUMENTS

| | | | | |
|---|---|---|---|---|
| 4,669,453 | A * | 6/1987 | Atkinson et al. | 601/161 |
| 4,793,807 | A * | 12/1988 | Friedman et al. | 433/80 |
| 4,887,554 | A * | 12/1989 | Whitford | 604/66 |
| 5,030,202 | A * | 7/1991 | Harris | 604/27 |
| 5,060,825 | A * | 10/1991 | Palmer et al. | 222/25 |
| 5,191,797 | A * | 3/1993 | Smith | 73/714 |
| 5,207,381 | A * | 5/1993 | Gill | 239/72 |
| 5,344,075 | A | 9/1994 | Springer et al. | |
| 5,383,605 | A * | 1/1995 | Teague | 239/526 |
| 5,560,317 | A * | 10/1996 | Bunyan et al. | 119/174 |
| 5,716,007 | A | 2/1998 | Nottingham et al. | |
| 5,735,959 | A | 4/1998 | Kubo et al. | |
| 6,217,328 | B1 * | 4/2001 | Oliver | 433/80 |
| 6,796,964 | B2 | 9/2004 | Eidson et al. | |

FOREIGN PATENT DOCUMENTS

| | | |
|---|---|---|
| AU | 499903 | 3/1978 |
| AU | 5489/80 | 7/1980 |
| AU | 524414 | 7/1980 |
| CA | 2267812 | 1/2000 |
| EP | 0 297 803 | 1/1989 |
| NZ | 242229 | 12/1994 |
| NZ | 248878 | 5/1997 |
| NZ | 260582 | 7/1997 |

* cited by examiner

*Primary Examiner*—Kevin Shaver
*Assistant Examiner*—James S. Hogan
(74) *Attorney, Agent, or Firm*—Hovey Williams LLP

(57) ABSTRACT

A liquid dispenser (100) primarily for use in dispensing liquid drench to animals. The dispenser (100) is electronic in operation and has the ability to control the speed of its pump (5) according to environmental conditions including the viscosity of the liquid being dispensed.

16 Claims, 3 Drawing Sheets

DEVICE FOR DISPENSING LIQUID

TECHNICAL FIELD

The present invention relates to a device for dispensing doses of liquid.

Reference throughout the specification shall be made to the use of the present invention in devices such as drench guns, injectors and the like that are used for treating livestock with liquid medicament. While the principles of the present invention could apply to other situations, it has been particularly developed for this field.

BACKGROUND ART

It is often desirable to treat livestock with drugs to control parasites. Parasiticides (or drenches) are often applied to the skin (as a pour-on liquid) or administered orally. Livestock may also be injected with these drugs. To control parasites, the livestock typically must be rounded up and placed in a holding area and separated by size so that each animal may be properly dosed with the drug. Once treated, the animal is released until the next dosing is required. Preferably a record is made of the drug and dose administered and the date of application.

Unfortunately, the process of separating the animals by size, administering the requisite dose to each size group of animals in turn and keeping manual records, is time consuming and expensive. This tempts the farmer into overdosing an animal to prolong the period during which the drug is present at effective levels. Furthermore, to avoid the sorting by size the farmer may rely upon his judgment to estimate the dosage to administer to each animal.

It should be appreciated that dispensing liquid in a farm environment is quite a different proposition to that in a more controlled situation such in a laboratory or factory.

Firstly, the environment in which the operator works is quite changeable.

For example, the reservoir holding the liquid (hereinafter referred to as drench) may be in a backpack on the operator. In other situations there may be a larger drench container situated on the ground, on a vehicle or elsewhere.

All these different environments can affect the operational dispensing device as the varying volumes, heights (which can affect pressure head) and container shapes and conduits to the dispensing outlet can lead to inconsistencies in the amount being dosed by the operator.

This is obviously an undesirable situation given that relatively precise doses of treatment liquid are required to ensure that the treatment is effective and the animal is either not overdosed or underdosed.

Another situation which is fairly specific to the drenching of animals is that quite often the same dispensing device is used to dispense a variety of treatment liquids, each having different viscosities or flow properties. Thus, it can take longer to dispense a certain volume of liquid having a high viscosity than the equivalent volume of a liquid having a low viscosity. This can be frustrating to the operator of the dispenser as often hundreds of animals are being treated at a time.

Whitford's New Zealand Patent No. 224789 describes a drench apparatus which attempts to overcome some of these difficulties by providing an animal scale with a weight transducer which supplies a signal used to regulate a motorised drench dosage pump to dispense a dose in proportion to the animal's weight.

A disadvantage with this system is the necessity of providing the scale, which is expensive and relatively massive. Not being readily portable it lacks versatility and does not lend itself to use away from the normal holding area on the farm, where it would typically be permanently installed. Moreover, this known system requires manual record keeping and provides no indication of the progress of the dispensing operation, such as the number of animals treated.

Eidson Associates' New Zealand Application No. 332852 also attempts to overcome a number of these problems by providing an automatic drenching system. This overcomes the problem of operator fatigue as an electronic switch on the hand held drench gun activates a peristaltic pump which pumps fluid through to the drench gun. However, this invention does not address a number of the problems in the prior art, including storage of information, changing environmental conditions, fluids of different viscosity and easy recalibration.

It is an object of the present invention to address the foregoing problems or at least to provide the public with a useful choice.

Further aspects and advantages of the present invention will become apparent from the ensuing description which is given by way of example only.

DISCLOSURE OF INVENTION

According to one aspect of the present invention there is provided a device for dispensing liquid which includes a hand piece for dispensing the liquid, a variable speed pump for pumping the liquid, and communication means which enables the operator of the device to alter the speed of the pump.

Reference throughout the specification should be made to the use of the device for dispensing the liquid for the treatment of animals in a farm situation. It should be appreciated however that he device can be used in other situations as well.

The liquid to be dispensed shall now be referred to as drench; however this should not be seen as a limitation on the use of the device.

The hand piece for dispensing the liquid should now be referred to as a drench gun. Again, this term should not be limiting and other hand pieces may be used including injectors and the like.

Preferably the drench gun is electronic in operation with an electronic trigger as well as a microprocessor for controlling the operation of the device.

In some embodiments the present invention includes a hand piece configured for use with the device.

In the preferred embodiment, the hand piece includes a trigger to actuate the dispenser, a keypad to enter data into the controller and a display. Preferably, the hand piece is lightweight and neutral to handedness, being equally amenable to left-hand or right-hand operation. A conduit connecting the hand piece to the pump may be retractable for convenience.

The variable speed pump is preferably a positive displacement pump. Preferably a gear pump is used as this has a number of advantages over other pumps. The applicant has found a gear pump which has acetyl gearing that is less susceptible to degrading through the chemical action of the drench passing through the pump. For example, peristaltic pumps require the use of soft tubing which can more readily degrade than harder plastics.

Another problem peristaltic pumps have in common with syringe pumps is that the liquid emerges in spurts over higher volumes. This is not a desirable characteristic for the operator of the device to cope with.

Syringe pumps also have the disadvantage in that they can also take longer than gear pumps to pump the same amount of volume.

Another advantage of gear pumps is that they can be produced in a small enough size to enable them to be readily carried by an operator in a backpack.

A further advantage of a gear pump is that it can be readily used to meter the amount of volume being dispensed.

Preferably, the variable speeds that the pump can operate are actually pre-programmed into a control system for the operation of the dispensing device.

The communication means may take a variety of forms. In one embodiment, the drench gun includes communication means that communicates with the control means of the pump or directly controls the pump. For example, the drench gun may include a transmitter which sends signals to the pump or pump controller.

However, in the preferred embodiments the drench gun is hard wired to the pump.

It is envisaged that in preferred embodiments, the operation of a trigger on the drench gun will cause the pump to operate thus dispensing fluid through to the drench gun. Preferably, the amount of volume being drenched can be selected by an operator through interaction with the software/electronics of the drench gun.

This selection process may be via a key pad and/or screen on the drench gun.

It is preferred that the initiation of the variable speeds of the pump would be via the operator interacting with the electronic drench gun. However, in some embodiments there may be a separate controller to that on the drench gun.

The operator may wish to change the speed of the pump under a number of circumstances.

For example, the operator may have previously been dosing animals using the device with the drench carried in a backpack. This may apply a certain pressure head to the system. Conversely, if the same dispensing device is used in accordance with a liquid reservoir situated on the ground there is no head of pressure. Therefore, in the latter situation it may be possible for liquid to flow back through the gear pump, thus delivering a lesser volume of drench than in the backpack situation over the same time.

Having regard to the foregoing, it would be an advantage to the operator to be able to increase the speed of the gear pump when the dispensing device is used in situations with low pressure heads to centre the effect of trickle back and give more uniform volumes over the same time.

In one embodiment of the present invention, the device may be programmed so that the operator may indicate to the device the environment (say via the drench gun) in which the device is working which causes the pump speed to adjust accordingly.

The drench gun may also be programmed for the operator to be able to indicate to the device the type of drench being dispensed, whether it be high, low or medium viscosity, or a proprietary drench. For example in some embodiments of the present invention particular drench names may be programmed into the drench gun.

Depending on the viscosity of the liquid identified as being dispensed, the pump speed may be operated by the controlling software of the device to ensure that the amount of time to dispense certain volume is substantially the same for the various liquids.

A table showing how parameters of the operation of the device can charge with different drenches is given below.

| DRENCH VISCOSITY | RPM |
|---|---|
| Low | 8,500 |
| Medium | 13,000 |
| High | 15,500 |

Having electronic controls associated with the device, and more preferably with the drench gun itself, a number of features can be built into the present invention.

In some embodiments the device may transmit data to or receive data from another device, for example an ear tag scanner, barcode reader, or a computerised farm management system. The data communicated may be control data relating to, for example, the requisite dosage for a particular animal or performance data such as a running total of volume of liquid dispensed.

It will be appreciated that the device may be adaptable to fully automate the keeping of records relating to animal drenching. In one embodiment, the software may provide means for downloading records to a computerised farm management system.

It should be further appreciated that in some embodiments a transceiver used within the present invention can be a mobile phone that can be used to connect to a modem or similar device in order to download data to a computer or in some cases upload data from the computer.

The present invention can also be readily used with electronic weigh scales which can give feedback to the controller and help calculate the volume of drench required for an animal of a certain weight.

Another aspect of the present invention there is provided a method of calibrating the volume of liquid dispensed by a device wherein the device includes a hand piece for dispensing liquid and a variable speed pump for pumping the liquid.

The method being characterised by the steps of a) inputting into the device a desired volume of liquid to be dispensed, and b) dispensing a volume of liquid from the device accordingly, and c) measuring independently the actual volume dispensed, and d) inputting into the device the actual volume dispensed or a comparative volume with the desired volume inputted in step a), and e) using the differential between the desired volume and actual volume to calibrate the operation of the device over a range of volumes.

It is possible that in between different operations and environments that slippage can occur with the desired volume as programmed into the device and the actual delivered volume. To address this the inventor has developed a calibration system as described above for calibrating the device at the start of an operation.

In preferred embodiments, the design of the device is such that calibration need only be undertaken once every day the device is being operated.

A significant advantage of the calibration method as described above is that only a single data point is required to be entered into the software of the device for recalibration to occur over a whole range of volumes. It can be appreciated that this can save considerable time.

Further, as the calibration method is implemented in software, there is no requirement for the operator to manually adjust settings on the pump or other valves in the system.

A preferred algorithm by which the calibration method is described above is given below

EXAMPLE 1

```
Procedure Calibrate
{This procedure will write the new calibration to the product memory, as well} {as set the current calibration to this selected product.}
Begin
  Beep;
  RdByteEE(LastProduct,Contents); (* Last product that was used is read from extended endurance memory *)
  IF Contents=255 THEN Contents:=3 (* Safety check to see if pointer to memory location is not out of range put it in current calibration position in memory. *)
  Else Contents:=(Contents*3)+6; (* calculate the location in extended endurance memory complete with offset relevant to current product in use *)
  Scratch:=ORD(Troix); (* find out if the amount is a positive amount or a negative amount. Increment the amount or decrement the amount. *)
  IF (Scratch=0) THEN Begin (* Three bytes were sent out. The third byte is the amount to correct, the second byte is the sign indication *)
    Alarm; (* if the amount to correct with is 0 than ignore the rest of this algorithm and exit here. *)
    EXIT;
  End;
  IF Scratch>=Lo(Dose) THEN Scratch:=Lo(Dose)−1; (* This statement protects and avoids the number that was entered was bigger than the original dose size. For example if a 10 ml dose was corrected by 12 ml, then the amount to correct with is larger than the original dose size
  IF ORD(Deux)=255 THEN Begin {255 indicates negative sign, 0 indicates positive sign *)
  IF (Dose>Scratch) Then Begin {only with a smaller correction}
    MyReal:=(((Dose+Scratch)/Dose)* 100)−100;
(* convert the calibration real number to the percentage reading. *)
  Calib:=Calib+((Calib/100)*MyReal); {increase the calibration}
  End {You can not subtract more than the dose}
  End Else Begin (* indicates a positive amount *)
    MyReal:=(((Dose+Scratch)/Dose)* 100)−100; {=Percentage more wanted}
    Calib:=Calib−((Calib/100)*MyReal); {Lower the calibration}
  End;
  Calib:=(Calib*100); (* conversion to the best fit 2 byte representation to store in EEPROM *)
  Handy:=Round(Calib); {Handy is a 16 bit word}
  WrByteEE(Contents,Hi(Handy)); {Copy the high byte}
  WrByteEE(CurrentCalib,Hi(Handy)); {Write calibration to EEPROM}
  WrByteEE(Contents+1,Lo(Handy)); {Copy the low byte}
  WrByteEE(CurrentCalib+1,Lo(Handy));
  WrByteEE(Contents+2,SetSpeed); (* Store the current speed setting with this calibration to recall back when read back again *)
  WrByteEE(CurrentCalib+2,SetSpeed);
  Calib:=Handy;
  Calib:=(Calib/100); (* Restore calibration value, a real number *)
  IF (Calib<0.1) Then Calib:=0.1; {safety not to go out of range in ridiculous values *)
  Dump(DipSwitch+80,Ord('c'),Ord('c')); (* Confirm calibration was done, send it to the gun and update it about which pump it came from.*)
End;
```

Most dispensing systems need priming at the start of any operation. In preferred embodiments of the present invention there is provided an automated priming routine controlled by the software of the device. In particular, gear pumps can have problems in priming air from a system. For example, in the present invention there may be an actuator such as button or a selection that the operator can make, say on the drench gun, at the start of any operation. Pressing the prime button could cause the pump to operate and any valves within the device to open allowing fluid to flow through conduits to the system and out the gun until all or most air is primed from the device. Activating the 'Prime' sequence could also ensure that any meters, counters or volume indicators are deactivated.

In some embodiments of the present invention there may be provided additional valving in the device to provide greater control of fluid flow and/or metering of fluid flow.

For example, in some embodiments there may be provided a valve situated between the drench reservoir and the pump. This valve (preferably a solenoid valve for accurate control) could perform the function of stopping excess trickle from the reservoir to the pump which can occur in particular when the present invention is used in a backpack situation.

In some embodiments there may be provided a flow valve associated with the drench gun. This valve can confirm whether actual drench has been dispensed. For example, the pump may operate and assume it is dispensing volume, but not be connected to the gun itself or may only be pumping air. The flow valve therefore provides more accurate metering.

The flow valve can also be used to stop problems of the trickle of liquid through the system on account of head pressure.

In preferred embodiments there is provided communication between the drench gun, pump and valves to ensure that the operation of each is coordinated appropriately to ensure the smooth delivery of the drench.

The hand piece may be adapted for applying a drench to the skin of an animal in a "pour-on" manner, and in one preferred embodiment of the invention a "pour-on" hand piece is used with a backpack mounted container and dispensing system.

Separate rechargeable batteries may be provided for power supply to both the power pack, comprising the motor/pump assembly and to the hand piece. Alternatively means may be provided for connecting the power pack to a suitable portable supply, such as the electrical system of a tractor.

It will be appreciated that the dispenser is particularly adapted for use administering drenches in either the pour on manner, orally or in injected form. The dispenser can be readily drained for changing from one medication to another and can also be quickly recalibrated to account for liquids of different viscosities.

BRIEF DESCRIPTION OF DRAWINGS

Further aspects of the present invention will become apparent from the following description which is given by way of example only and with reference to the accompanying drawings in which.

BEST MODES FOR CARRYING OUT THE INVENTION

Figure 1:
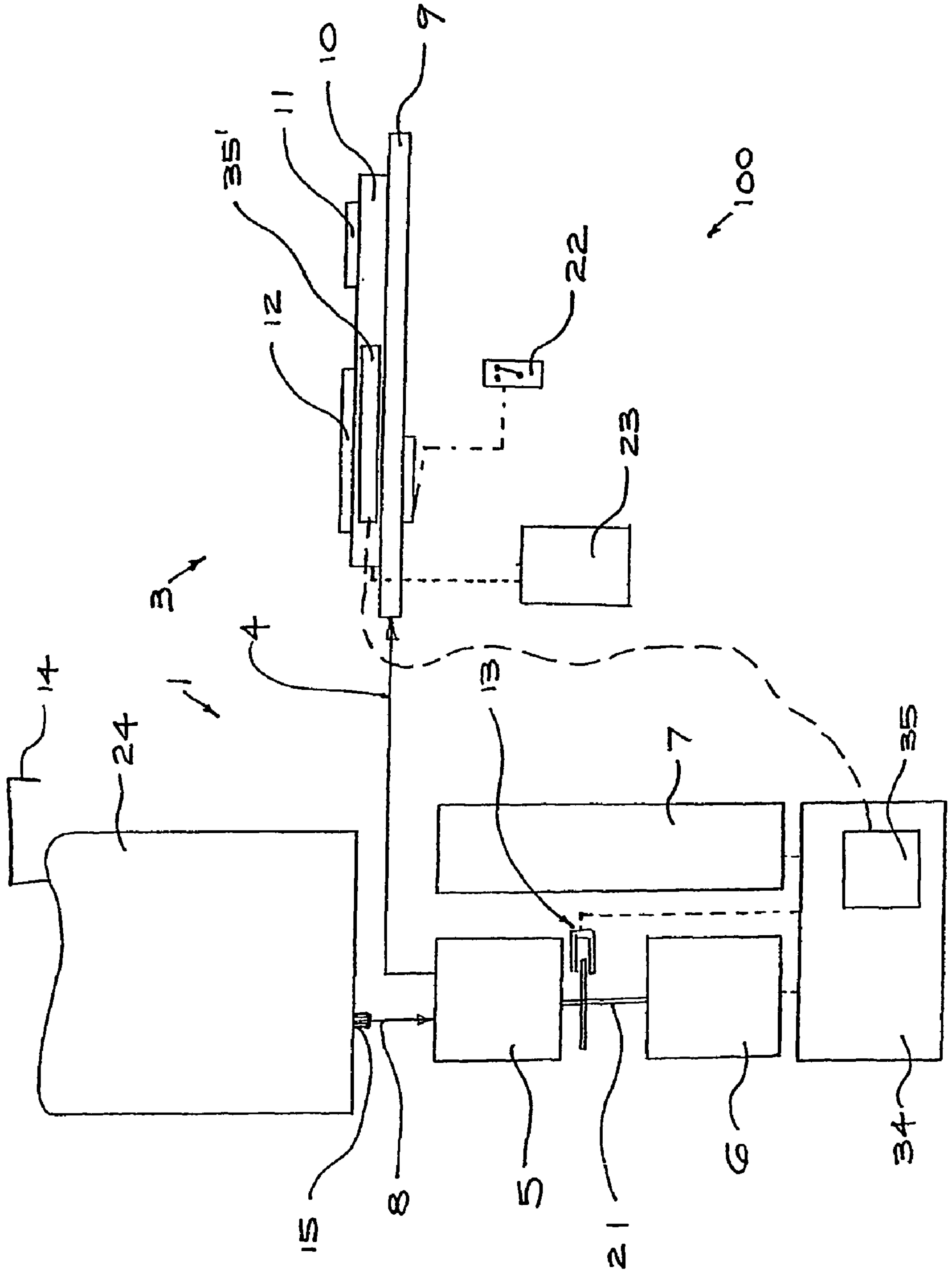
FIG. 1 is a schematic of the metered liquid delivery device of the present invention.

In FIG. 1 electrical/magnetic (including possibly wireless) connections between components are represented by dashed lines, while liquid connections are represented by solid lines. The metered liquid delivery device 100 includes two main sub-components, power pack 1 and hand piece 3 connected by discharge hose 4. A container 24, in which is kept a liquid drug composition is connected to the power pack 1. The container 24 could be any number of devices including a tank mounted on a tractor, an easily portable twenty-litre container or a back pack mounted container or the like. The container 24 has an atmospheric vent 14 and a coupling 15.

The liquid in the supply container 24 is pumped by a gear pump S, driven by a motor 6. Optionally, the motor 6 may include a reducer gear (not shown) to match the motor 6 speed to the pump 5 requirements and the motor may be reversible. Electrical power is provided to the power pack 1 components through a battery 7, or in alternative embodiments another power supply such as the mains.

The liquid is drawn from the supply container 24 through a suction hose 8 by the gear pump 5 and then pumped through a discharge hose 4 to a restrictor valve 9 on the outlet of the hand piece 3. The restrictor valve 9 is a flow control valve, of a normally closed spring-loaded type which is opened by the pressure of the liquid in the hose 4 and closes when the pressure is reduced. Alternatively, the restrictor valve 9 may be of a solenoid-operated type.

The dispensing operation is controlled by a microprocessor-based electronic controller which is mounted on the hand piece 3, having an associated slave circuit 34 on the power pack 1. The controller 10 and circuit 34, both include transceivers 35, 35' respectively for wireless communication there between, preferably in the UHF band. In some instances it may be desirable, however, to use a wired connection. Electrical power is provided to the hand piece 3 components through a battery 23. Alternatively, if a wired connection is provided, power may be supplied from the power pack and the battery 23 may be omitted.

The user enters specific data concerning a particular dispensing operation into the controller 10 by means of a keypad 12 on the hand piece 3. The hand piece 3 also includes a trigger 22 to actuate the dispenser 100. The controller 10 also has an alphanumeric display 11 to prompt the user through the associated program, and to provide information to the user during the dispensing operation. As will be discussed, the controller 10 monitors various system operating parameters, and controls the operation of the motor 6 to achieve a desired pre-programmed dispensing operation.

A precisely known volume of liquid is displaced with each revolution or fraction of revolution of the pump drive shaft 21. A transducer 13 is coupled to sense the rotation of the pump drive shaft 21 and provide this information to the electronic controller 10 via the circuit 34 and transceivers 35, 35'. Once the system 100 is primed, the controller 10 is then able to precisely control the amount of dispensed liquid by monitoring the rotation of the drive shaft 21. The transducer 13 can be one of several types such as a passive variable reluctance magnetic transducer, or a Hall effect device.

In operation the user first connects the container coupling 15 to the user's container 24. The electronic controller 10 initiates a series of system diagnostics and if any of the diagnostics fail, an error message is displayed on the display 11 and the controller 10 is disabled Prior to recording the amount of liquid being pumped, the discharge hose 4 must be primed. During priming of the discharge hose 4, air within the hose 4 is forced through the restrictor valve 9, and this volume of air will not be applied to the desired dose amount. The hose 4 is preferably reasonably short, as when it is fitted to a back pack mounted container (not shown) for use in the field. The hose 4, however, may be lengthy, as when used with a remotely located container. The priming may be accomplished by pressing a prime button (not shown) on the power pack 1 which causes the pump 5 to run. As the discharge hose 4 fills with fluid, air is displaced through the restrictor valve 9 into the atmosphere. Once the prime is detected visually by the user, who can see liquid being ejected, a signal is sent to the electronic controller 10, the gear pump 5 is stopped, and the integrity tests continued. Alternatively, means such as a reed switch (not shown) may be employed to sense the presence of liquid and indicate this to the controller 10.

After successfully completing all the system integrity tests, the display 11 will indicate the dispenser 100 is ready for operation. The user now is able to scroll the display 11 through a menu of pre-programmed functions. He may enter a dose size, a dose (or discharge) rate, and other such functions as allowing for the volume units displayed to be changed. Once the correct dose amount has been entered, the trigger 22 is pressed to dispense the liquid. The controller 10 starts the motor 6 and the gear pump 5 begins to pump liquid from the container 24. As previously mentioned, the transducer 13 senses the rotation of the gear pump drive shaft 21 and transmits the information to the controller 10 which records the volume of liquid being pumped, the controller 10 stopping the transfer when the desired does has been dispensed The controller 10 may be recalibrated if a fluid of a different viscosity is to be pumped. The supplier can also zero a running total which is held in the control memory unit and may include the total number of doses and their volume since the counter was last reset.

A drain cycle may be initiated by the user to drain the line, in order that the system may be used to deliver a different liquid. The inlet hose 8 is disconnected by way of the coupling from the container 24, and the motor 6 is then run (by pressing the prime button (not shown) on the power pack 1) to draw air through the pump 5 and thereby displace the liquid from the hose 4. As when priming the device 100, the user may direct the liquid into the container 24.

Figure 2:
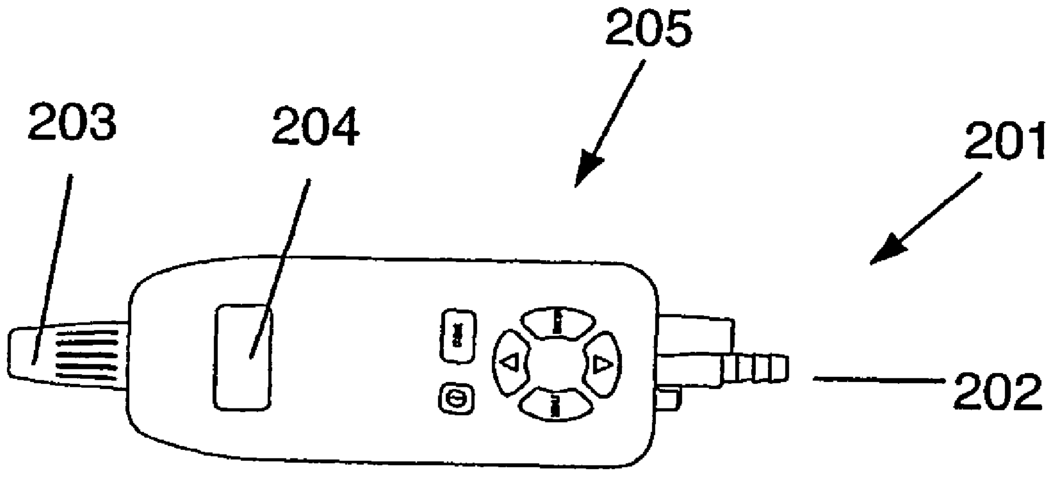
FIG. 2 is a diagrammatic top view of a drench gun in accordance with one embodiment of the present invention.

FIG. 2 illustrates the top view of one embodiment of a drench gun in accordance with the present invention.

The drench gun 201 has an inlet 202 which receives liquid received by the pump, and an outlet 203 which is attached to an appropriate nozzle, needle and the like.

The top of the drench gun has a screen 204 which can display various information and menus allowing the operator to select modes of operation in the like.

A number of keys generally indicated by arrow 205 enable the operator to enter information and select control functions from a menu as required.

Figure 3:
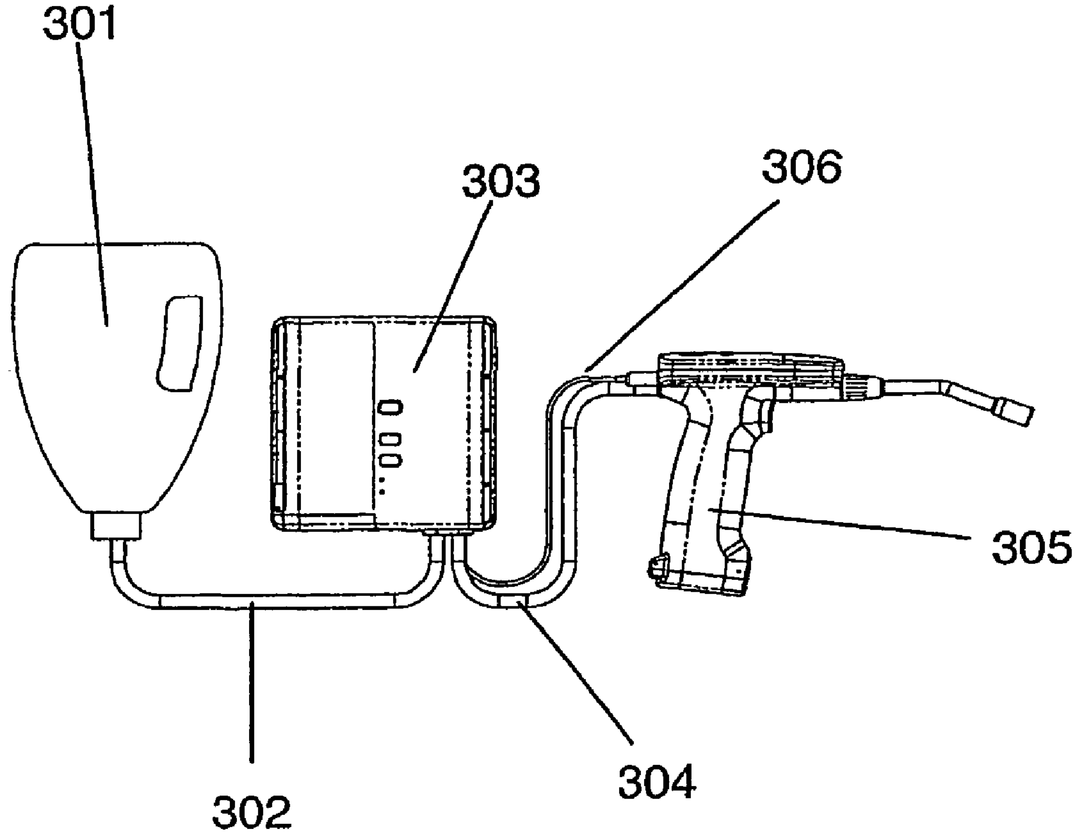
FIG. 3 is a diagrammatic view of a drench container, pump and drench gun in accordance with one embodiment of the present invention.

FIG. 3 is a diagramatic representation showing the connection of a back pack drench reservoir 301 connected by tubing 302 to a pump 303. The length of the tubing is not representative of actual lengths which may vary considerably.

The pump 303 is connected by a tubing 304 to the inlet of the drench gun 305. An electronic connection 306 is also present between the drench gun 305 and the pump 303. This electronic connection is a means by which the drench gun conveys control operations to the pump.

Aspects of the present invention have been described by way of example only and it should be appreciated that modifications and additions may be made thereto without departing from the scope of the appended claims.

The invention claimed is:

1. A device for dispensing liquid which includes a hand piece for dispensing the liquid, a variable speed pump for pumping the liquid, communication means which enables the operator of the device to alter the speed of the pump to any one of a number of pre-programmed variable speeds, and a controller having an automated priming routine, wherein the hand piece includes a screen, and wherein a valve is situated between a fluid reservoir connected to the device and the pump.

2. A device as claimed in claim 1 wherein the liquid is drench.

3. A device as claimed in claim 1 wherein the hand piece is a drench gun.

4. A device as claimed in claim 1 wherein the pump is a positive displacement pump.

5. A device as claimed in claim 4 wherein the pump is a pump gear.

6. A device as claimed in claim 1 wherein the hand piece includes the communications means.

7. A device as claimed claim 1 wherein the hand piece includes a key pad.

8. A device for dispensing liquid as claimed in claim 1 which further includes control means for enabling the operator to indicate to the device the environment in which the device is operating whereby the pump speed is caused to be adjusted accordingly.

9. A device as claimed in claim 8 including control means for enabling the operator to indicate to the device a type of liquid to be dispensed whereby the pump speed is caused to be adjusted accordingly.

10. A device as claimed in claim 9 wherein the type of liquid is chosen according to viscosity.

11. A device as claimed in claim 10 wherein the type of liquid is chosen according to pre-programmed names.

12. A device as claimed in claim 8 which can transmit and receive data.

13. A device as claimed in claim 12 which includes a mobile phone.

14. A device as claimed in claim 1 including volume indicators, wherein during the priming routine volume indicators on the device are deactivated.

15. A device as claimed in claim 1 including a flow valve associated with the hand piece.

16. A method of calibrating the volume of liquid dispensed by a device as claimed in claim 1, comprising the steps of:

a) inputting into the device a desired volume of liquid to be dispensed;

b) dispensing a volume of liquid from the device accordingly;

c) measuring independently the actual volume dispensed;

d) inputting into the device the actual volume dispensed or a comparative volume with a desired volume inputted in step a); and e) using the differential between the desired volume and the actual volume to calibrate the operation of the device over a range of volumes.

* * * * *